US006235002B1

(12) United States Patent
Carver, Jr. et al.

(10) Patent No.: US 6,235,002 B1
(45) **Date of Patent: *May 22, 2001**

(54) SYRINGE FOR USE IN FLUID-HANDLING APPARATUS

(75) Inventors: Edward Lawrence Carver, Jr., Oxford; Frank Antoci, Stratford, both of CT (US)

(73) Assignee: CDC Technologies, Inc., Oxford, CT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/062,107

(22) Filed: Apr. 17, 1998

(51) Int. Cl.[7] .................................................... A61M 5/178

(52) U.S. Cl. ............................................ 604/183; 604/122

(58) Field of Search ............................ 604/181, 122–125, 604/131, 150, 173, 183, 194, 218, 231, 235, 187, 151, 152, 154, 221, 222, 236, 207, 68; 141/2, 18

(56) References Cited

U.S. PATENT DOCUMENTS 701,671 6/1902 Billings .
2,771,880 11/1956 Gotthart .
2,893,391 7/1959 Vlasic .
3,279,659 * 10/1966 Harris, Jr. ............................ 222/387
3,401,692 9/1968 Harris, Jr. .
4,275,730 6/1981 Hussein ............................... 128/234
4,690,154 9/1987 Woodford et al. .
4,842,581 6/1989 Davis .................................... 604/38
4,950,243 8/1990 Estruch ............................... 604/110
5,019,045 5/1991 Lee ...................................... 604/110
5,030,002 7/1991 North, Jr. .
5,380,491 1/1995 Carver, Jr. et al. .
5,769,824 * 6/1998 Hjertman et al. .................... 604/143
5,882,343 3/1999 Wilson et al. ....................... 604/246

* cited by examiner

*Primary Examiner*—Richard K. Seidel
*Assistant Examiner*—LoAn H. Thanh
(74) *Attorney, Agent, or Firm*—Cummings & Lockwood

(57) ABSTRACT

An improved displacement-type syringe has a housing, a substantially fixed seal, a solid or closed-tip plunger, an internal passageway formed between the housing and the plunger, and at least two ports on the housing with at least one port located at each end of the passageway for the passage of fluids and the elimination of gas. The syringe may be mounted in apparatus over a wide range of fixed inclination angles and remain substantially impervious to gas accumulation.

19 Claims, 4 Drawing Sheets

SYRINGE FOR USE IN FLUID-HANDLING APPARATUS

TECHNICAL FIELD

The present invention relates to an improved syringe, and in particular, to an improved displacement-type syringe comprising at least one port at each end of the syringe which are connected in fluid communication via an axially-elongated passageway, the syringe being particularly suitable for use in apparatus for hematological analysis and/or particle counting.

BACKGROUND INFORMATION

Typically, a syringe comprises a hollow syringe cylinder which is open at a first end to accept a plunger, and which includes an axial port at a second end through which fluids may pass. The plunger may be of the forced discharge or of the displacement type, the displacement type having an intentional significant gap between the plunger and the syringe cylinder.

The forced discharge type of syringe relies mainly on a pressure differential between the syringe contents and the discharge port in order to force out the contents. Unfortunately, this type of syringe may display a non-linear relationship between plunger rate and discharge rate due in part to internal fluid dynamics, especially near the extremes of plunger travel. The displacement type of syringe generally displays a more linear relationship between plunger rate and discharge rate.

A common goal with many types of syringes is to eliminate gas within the hollow syringe cylinder. Displacement-type syringes may be generally more susceptible to gas build-up than other types mainly because of the substantial non-displaced volume remaining within a displacement-type syringe even at full plunger travel.

Syringes mounted in fluid-handling apparatus, such as apparatus for hematological analysis and/or particle counting, may be especially plagued by gas build-up due to the inability to conveniently reorient and reposition the syringe in order to expel a gas bubble. A significant problem with gas bubbles is that they act as pressure and vacuum reservoirs which especially reduce the displacement accuracy of the syringe. In addition, expelling the gas from a syringe mounted downwards may be nearly impossible with many prior art fluid-handling apparatus.

Accordingly, it is an object of the present invention to facilitate an improved displacement-type syringe suitable for mounting in fixed, fluid-handling apparatus and which overcomes the above-described drawbacks and disadvantages of the prior art.

SUMMARY OF THE INVENTION

The present invention is directed to a syringe comprising a syringe housing, a plunger slidably received within the syringe housing, and a longitudinally-extending passageway formed between the plunger and syringe housing. A fixed seal is mounted at approximately one end of the longitudinally-extending passageway, and the plunger is slidably received and movable through the seal to displace fluid into and out of the syringe housing. At least one fluid port is located at approximately one end of the longitudinally-extending passageway, and at least one other fluid port is located at approximately the other end of the passageway in fluid communication with the other fluid port to permit the flow of fluid and gas into and out of the passageway regardless of the orientation of the syringe. Thus, the plunger displaces a known volume of fluid corresponding to its volumetric displacement, but otherwise leaves fluid within the syringe passageway. Any gas or bubbles left within the passageway are permitted to flow out through one or both fluid ports at either end of the passageway to thereby maintain the syringe in a gas-free state.

One advantage of the invention is that the syringe may be mounted at any angle of inclination including horizontally (although a substantially horizontal orientation, having an inclination of approximately two to five degrees, is preferred), and still be substantially impervious to gas accumulation. Thus the syringe will remain accurate over a wider range of fixed mounting positions than permitted under the prior art.

Another advantage is that the seal which is fixedly mounted at one end of the longitudinally-extending passageway has the smooth plunger as its only sliding surface, thus reducing friction, wear, and distortion in comparison to prior art syringes that may slide a seal against the inside surface of a syringe housing. Thus the seal is subjected to lower friction than a moving seal in a typical prior art syringe, resulting in lower wear, longer life, less seal distortion, and/or higher accuracy.

Other advantages of the present invention will become apparent in view of the following detailed description and accompanying drawings.

BRIEF DESCRIPTION OF THE DRAWINGS

The invention will now be described by way of example with reference to the drawings in which.

DETAILED DESCRIPTION OF THE PREFERRED EMBODIMENT

Figure 1:
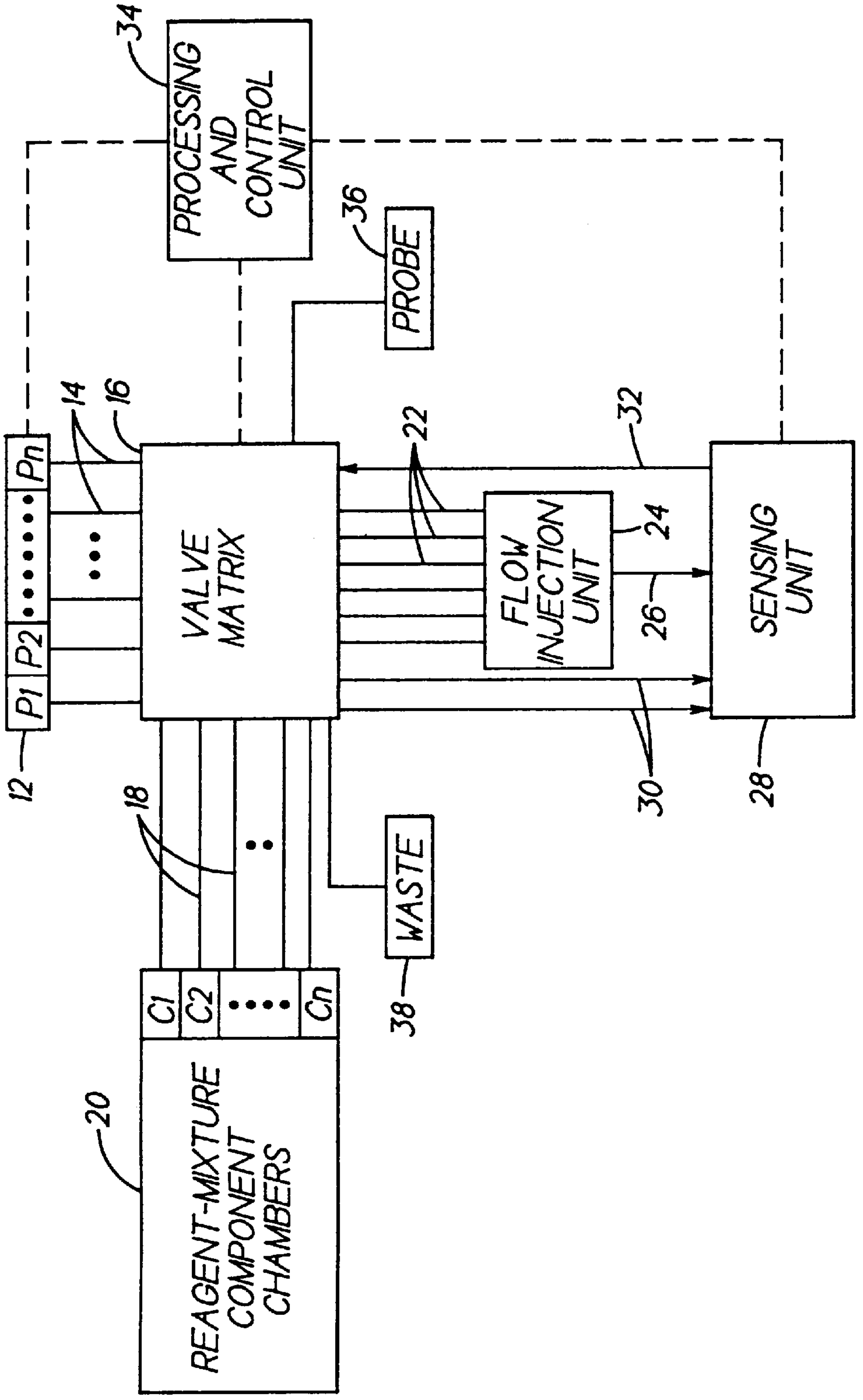
FIG. 1 is a block diagram of an apparatus embodying the present invention for hematological analysis and/or particle counting.

In FIG. 1, a fluid-handling apparatus for hematological and/or particle counting is indicated generally by the reference numeral 10. The apparatus 10 comprises a plurality of positive-displacement pumps 12, each in the form of a syringe embodying the present invention and indicated schematically in FIG. 1 as P1, P2 . . . Pn. The plurality of syringes 12 are coupled in fluid communication through a plurality of pump lines 14 to a valve matrix 16. The valve matrix 16 is of a type known to those of ordinary skill in the pertinent art and connects the various fluid-handling components of the apparatus in fluid communication with each other to control the direction and flow of reagent-mixture components and other fluids, if necessary. The valve matrix 16 is connected through a plurality of lines 18 to a bank of reagent-mixture component chambers 20, indicated schematically in FIG. 1 as C1, C2 . . . Cn. Each chamber 20 is adapted to receive a respective reagent-mixture component, such as a whole blood sample, diluent, membrane-modifying reagent, or diluted blood sample. If necessary, one or more chambers 20 may contain other fluids to be used, for example, to rinse or wash conduits and other fluid-handling components of the apparatus.

The valve matrix 16 is also connected through a plurality of injection lines 22 to a flow-injection unit 24 for injecting at least one reagent-mixture component into a stream of at least one other reagent-mixture component in order to thoroughly and uniformly mix the components and create a selected reagent mixture. The flow injection unit 24, and a preferred method of forming and analyzing the reagent mixtures, are disclosed in further detail in U.S. patent application Ser. No. 08/458,701, filed Jun. 2, 1995, now U.S. Pat. No. 5,840,254, entitled "Apparatus And Method For Mixing Fluids For Analysis", and in U.S. patent application Ser. No. 08/854,377, filed May 12, 1997, now U.S. Pat. No. 5,907,240 entitled "Method and Apparatus for Cell Differentiation by Measuring Apparent Cell Size, Membrane Integrity and Intracellular Complexity", each of which are assigned to the Assignee of the present invention, and are hereby expressly incorporated by reference as part of the present disclosure.

The flow injection unit 24 is coupled through a reagent-mixture injection line 26 to a sensing unit 28 defining a sensing orifice for receiving the reagent-mixture. As described in the above-mentioned co-pending patent application, the sensing unit 28 preferably applies a predetermined dc voltage across the sensing orifice to thereby create a dc electric field, and is responsive to the passage of sample cells through the orifice to sense a change in at least one property of the dc electric field, and in turn generate based thereon for each cell a signal indicative of the size, membrane integrity and intracellular complexity of the respective cell. However, as will be recognized by those skilled in the pertinent art based on the teachings herein, numerous other types of known sensing units equally may be employed which may count the cells and measure their size and/or opacity by sensing, for example, electrical or optical differences. Accordingly, the sensing unit 28 may also embody the teachings of U.S. Pat. No. 5,380,491, and U.S. Pat. No. 5,728,351 which is a divisional of U.S. Pat. No. 5,380,491, both of which are assigned to the Assignee of the present invention and are hereby expressly incorporated by reference as part of the present disclosure.

One or more secondary injection/aspiration lines 30 are coupled between the valve matrix 16 and sensing unit 28 for pumping other fluids to the sensing unit, including, for example, diluent sheaths surrounding the reagent-mixture stream. One or more return lines 32 are also coupled between the sensing unit 28 and valve matrix 16 for receiving fluids from the sensing unit, including, for example, the reagent mixture and diluent sheath surrounding the reagent mixture.

As also shown in FIG. 1, a processing and control unit 34 is coupled to each of the syringes 12, the valve matrix 16 and sensing unit 28 to control operation of each component, analyze the data, and provide analysis results. The processing and control unit 34 is preferably constructed to operate in accordance with the teachings of U.S. Pat. Nos. 5,187,673 and 5,349,538, both of which are assigned to Edward L. Carver, Jr., and are hereby expressly incorporated by reference as part of the present disclosure. The syringes 12 may be independently actuated and controlled by the processing and control unit 34, to in turn control the volumes and flow rates of the fluids being injected or aspirated by the pumps.

As also shown in FIG. 1, the apparatus 10 may further comprise a probe 36 coupled to the valve matrix 16 for aspirating the various fluids through the valve matrix and introducing the fluids into the various reagent-mixture component chambers 20. A waste chamber 38 is also coupled to the valve matrix 16 for receiving the fluids after passage through the sensing unit 28, and any other fluids in the apparatus to be discarded as waste.

Figure 2:
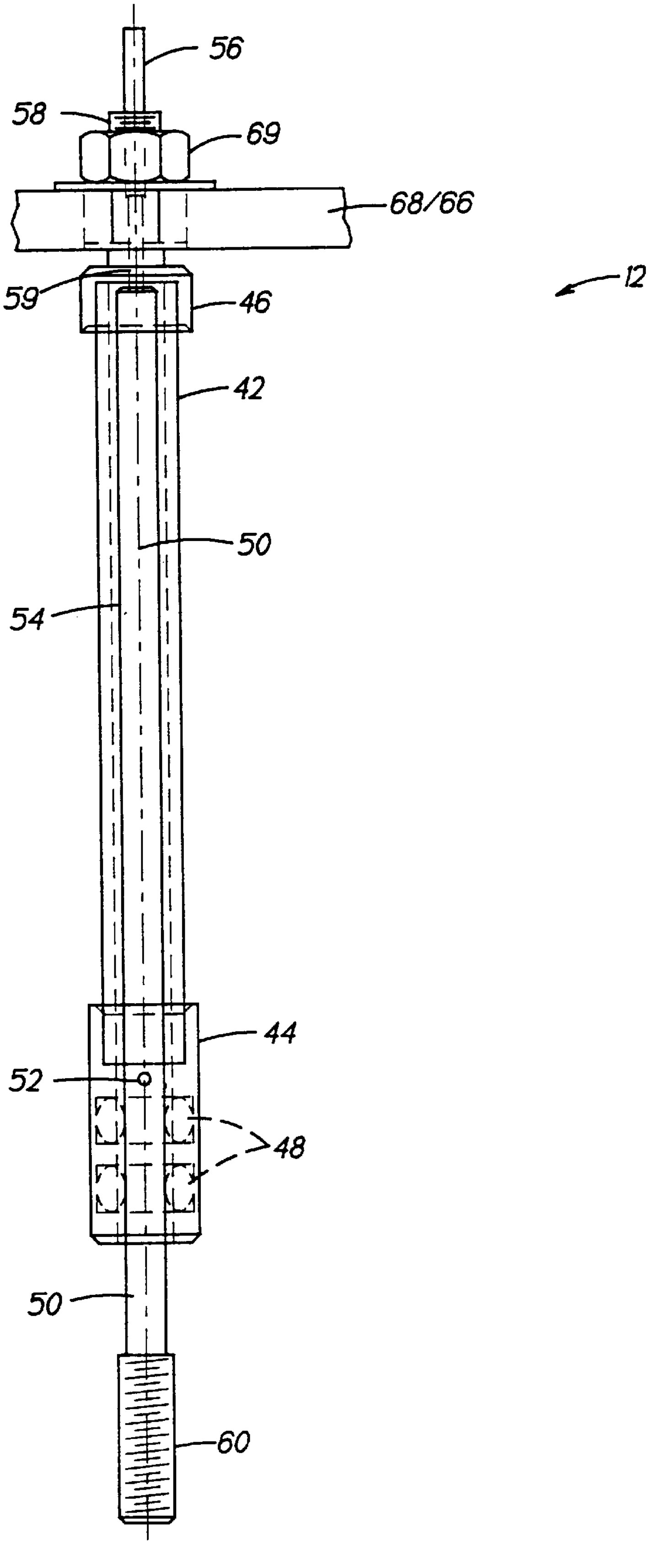
FIG. 2 is a side elevational view of a syringe embodying the present invention.

With reference to FIG. 2, a typical syringe 12 of the invention comprises a tubular housing 42, a first connector or fitting 44 fixedly secured at one end of the housing, and a second connector or fitting 46 fixedly secured at the other end of the housing. The first fitting 44 at the first end houses a seal 48 formed by two captive o-rings through which a piston or plunger 50 slides, as well as a radial port 52 in fluid communication with an internal longitudinally-extending fluid passageway 54. The fluid passageway 54 is formed by an annular space between the plunger 50 and the tubular housing 42, and extends from approximately one end of the syringe to the other. The second fitting 46 at the second end comprises an axial port 56 in fluid communication with the fluid passageway 54 and a threaded portion 58 for fixedly mounting the syringe within the apparatus 10, as is described further below. Thus, as shown in FIG. 2, the longitudinally-extending fluid passageway 54 provides a means for maintaining the radial port 52 in fluid communication with the axial port 56 for all intermediate positions of the plunger 50. As also as shown in FIG. 2, the plunger 50 defines on its end located within the tubular housing 42 a beveled or tapered tip, and the second fitting 46 defines an aperture 59 for receiving the tapered tip of the plunger when located at the inner end of its stroke to thereby effect a substantially fluid-tight seal between the plunger and fitting. A threaded collar 60 is fixedly secured to the external end of the plunger 50 for drivingly connecting the plunger to a motor within the apparatus 10, as is described further below.

As shown in FIG. 2, the axial port 56 is in fluid communication with the radial port 52 by means of the axially-elongated passageway 54 extending between the two ports and defined within the axially-elongated, annular space between the plunger 50 and tubular housing 42. Thus, the elongated passageway 54 forms an unobstructed path for the flow of fluid and gas between the entire syringe contents and the axial and radial ports to thereby permit undesirable gas to be expelled with the syringe mounted in an apparatus at almost any angle of inclination.

In the operation of each syringe 12, fluid is drawn into the syringe by retracting the plunger 50 out of the housing 42 (i.e., the outer stroke of the plunger, which is downwardly in the syringe orientation of FIG. 2). The plunger 50 defines a solid exterior surface, and thus defines a volumetric displacement within the housing 42 corresponding to the degree to which the plunger is moved into or out of the housing. Accordingly, when the plunger 50 is retracted from the housing 42, a volume of fluid is drawn into the housing which is approximately equal to the volumetric displacement of the portion of the plunger withdrawn from the housing. The fluid may be drawn into the syringe through the axial port 56 and/or the radial port 52. However, in the preferred mode of operation, the fluid is drawn into the lower port (which may be either the axial or the radial port, depending upon the syringe orientation), and expelled through the upper port. In this way, any gas bubbles drawn into the syringe will flow to the upper portion of the internal passageway 54, and may be expelled from the syringe with the next inward stroke of the plunger 50. Fluid is then injected out of the syringe 12 by moving the plunger 50 inwardly of the housing 42 (or upwardly in the orientation of FIG. 2). The volume of fluid ejected from the syringe is approximately equal to the volumetric displacement of the portion of the plunger 50 moved into the syringe. The fluid may be ejected from the syringe through either the axial port 56 or radial port 52 by controlling the valve matrix 16 to open the selected port and close the other. However, as described above, fluid is preferably ejected from the syringe through the upper port (which may be either port depending upon the orientation of the syringe) in order to facilitate the removal of any undesirable gas from the elongated passageway 54.

Figure 3:
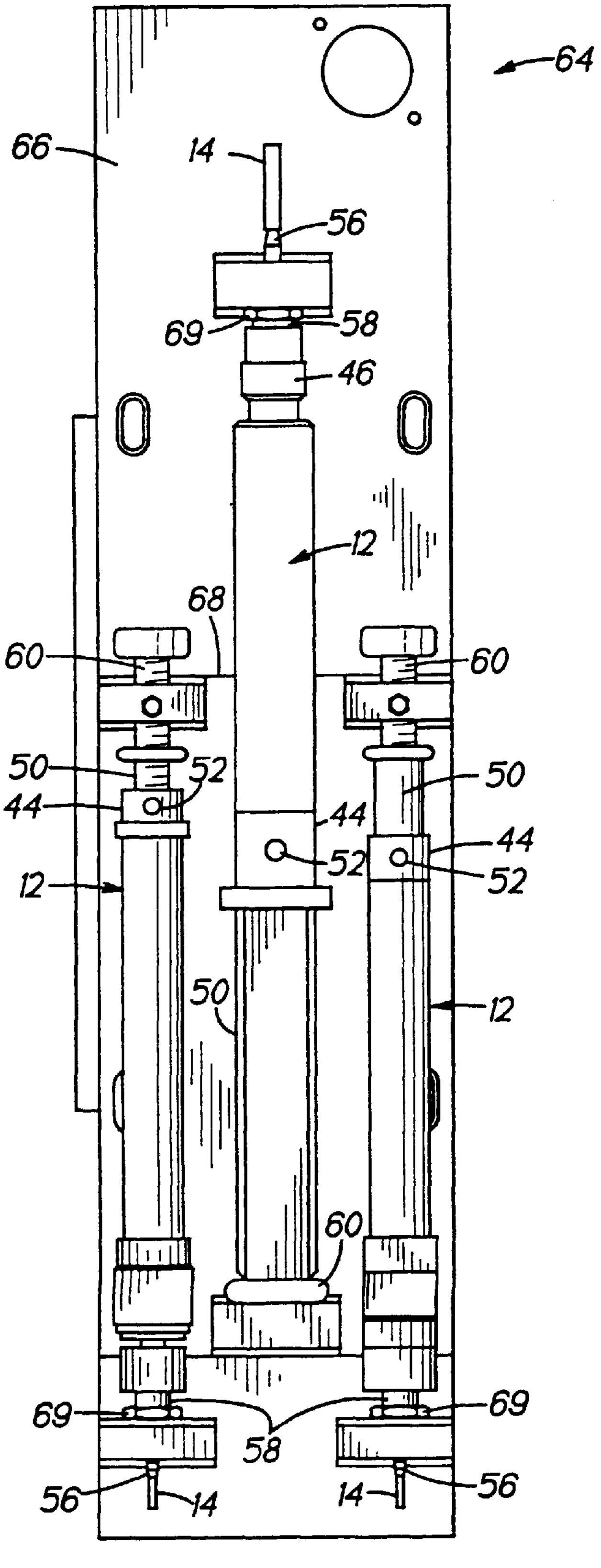
FIG. 3 is a front elevational view of a pump unit of the apparatus of FIG. 1, comprising three syringes of the type illustrated in FIG. 2.
Figure 4:
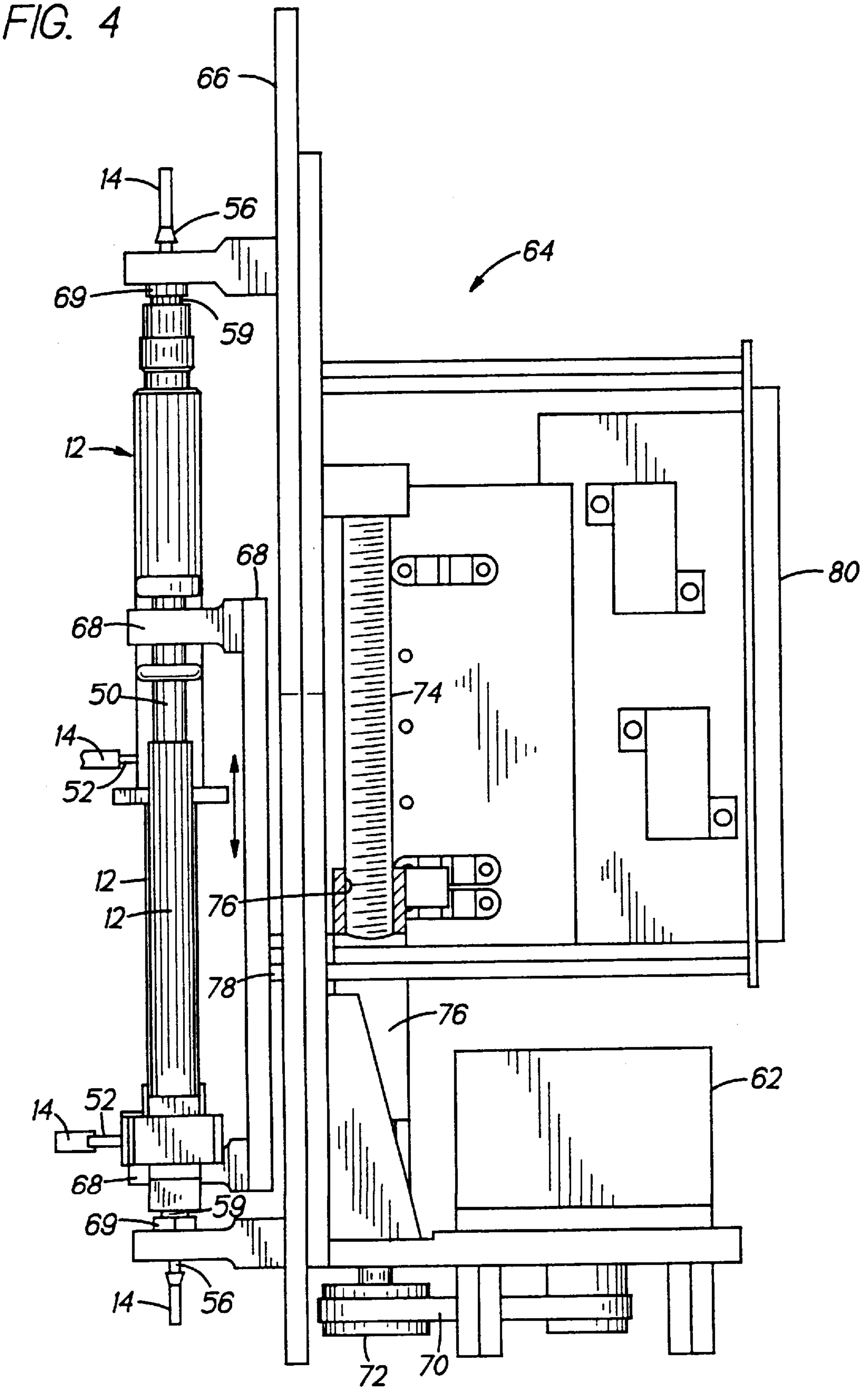
FIG. 4 is a side elevational view of the pump unit of FIG. 3.

With reference to FIGS. 3 and 4, the currently-preferred apparatus 10 comprises three syringes 12 mounted together and driven by a common motor 62 (FIG. 4) to form a pump unit 64. The pump unit 64 comprises a base plate 66 and a drive plate 68 which is driven by the common drive motor 62 relative to the base plate to move the plungers 50 and thereby aspirate and inject fluid into and out of the three syringes. As shown best in FIG. 3, two of the syringes 12 are mounted with the threaded portions 58 of their second fittings 46 fixedly secured to the lower end of the base plate 66, and the threaded collars 60 of their plungers 50 fixedly secured to the upper end of the drive plate 68. AS shown typically in FIG. 2, each threaded portion 58 is fixedly secured to the base plate by a threaded nut or like fastener 69. As shown in FIG. 3, the axial and radial ports 56 and 52, respectively, are each connected to one end of a pump line 14 to pump selected fluids through the valve matrix 16. Accordingly, movement of the drive plate 68 upwardly in FIGS. 3 and 4 causes the plungers 50 of these two syringes to move out of the respective housings 42 and thereby draw a volume of fluid into each syringe corresponding to the volumetric displacement of the portions of the plungers withdrawn from the housings. Movement of the drive plate 68 downwardly in FIGS. 3 and 4, on the other hand, causes the plungers 50 of these two syringes to move back into the housings 42 and thereby eject a volume of fluid out of each syringe corresponding to the volumetric displacement of the portion of each plunger moved into each housing.

As also shown best in FIG. 3, the third syringe 12 is mounted between the other two syringes, with the threaded portion 58 of its second fitting 46 fixedly secured by a nut or like threaded fastener 69 to the upper end of the base plate 66, and the threaded collar 60 of its plunger 50 fixedly secured to the lower end of the drive plate 66. Accordingly, movement of the drive plate 68 upwardly in FIG. 3 causes the plunger 50 of the third (or middle) syringe 12 to eject fluid from the syringe, and movement of the drive plate downwardly in FIG. 3 causes the plunger 50 to draw fluid into the third syringe. The axial and radial ports 56 and 52, respectively, of the third (or middle) syringe 12 are likewise each connected to a respective pump line 14 to pump selected fluids into and out of the syringe through the valve matrix 16.

As shown in FIG. 4, the drive motor 62 is drivingly connected by a drive belt 70 to a pulley or gear 72 keyed to one end of a threaded drive shaft 74 to rotatably drive the shaft. A drive block 76 is threadedly mounted to the drive shaft 74 to move up and down the shaft depending upon the direction of rotation of the motor and shaft. The drive block 76 is connected by drive mounts 78 to the drive plate 68 to move the drive plate, and thus the plungers 50 of the syringes 12 upon actuating the drive motor 62. The drive motor 62 is electrically connected to a control board 80, which in turn is electrically connected to the processing and control unit 34 to control the operation of the motor 62 and syringes 12.

One advantage of the syringe of the present invention is that any axial port 56 or radial port 52 may be used for input and/or output of fluids, and the syringes may be mounted within an apparatus with their elongated axes mounted in virtually any angular orientation between vertical and substantially horizontal without accumulating gas within the syringe. In each case, the port chosen for output should be one which is at least as high as any other portion of the elongated passageway 54. Accordingly, another advantage of the present invention is that the syringe is substantially impervious to gas accumulation, and therefore will remain accurate over a wider range of fixed mounting positions than permitted under the prior art.

Yet another advantage of the preferred embodiment of the invention is that the o-ring seal(s) are fixedly mounted within the fitting at one end of the tubular housing, with the smooth plunger slidably mounted within the fixed seal, thus reducing friction, wear, and distortion in comparison to prior art syringes that may mount the seal(s) on, and movable with the plungers. Thus the o-rings are subjected to lower friction than a typical moving seal, resulting in lower wear, longer life, less seal distortion, and/or higher accuracy.

As will be recognized by those skilled in the pertinent art, numerous modifications may be made to these and other embodiments of the present invention without departing from the scope of the invention as defined in the claims. For example, the syringe may include radial ports at both ends of the tubular housing, and a conduit may be located external of the housing and coupled in fluid communication between the two ports for permitting gas to flow out of at least one of the two ports regardless of the syringe's orientation. Accordingly, this detailed description of a preferred embodiment is to be taken in an illustrative rather than a limiting sense.

What is claimed is:

1. A syringe comprising:

an elongated housing defining a side wall, and an axially-elongated fluid passageway having a first end and a second end and extending through a substantial portion of the housing in an axial direction thereof;

at least one first fluid port located at approximately the first end of the passageway and coupled in fluid communication therewith for permitting the flow of fluid and gas into and out of the passageway;

at least one second fluid port located at approximately the second end of the passageway and coupled in fluid communication with the passageway and the first fluid port for permitting the flow of fluid and gas into and out of the passageway;

a plunger slidably received and movable through the housing between the first and second fluid ports for moving fluid into and out of the housing, wherein the axially-elongated passageway is formed between the plunger and the side wall of the housing and defines an unobstructed fluid-flow path connecting the first and second fluid ports in fluid communication with each other with the plunger located therebetween, to thereby allow gas within housing to flow out through at least one of the first and second fluid ports and prevent an accumulation of gas within the housing; and a seal mounted on the housing and located between the at least one first fluid port and an adjacent end of the housing.

2. A syringe as defined in claim 1, wherein the plunger defines a solid exterior surface.

3. A syringe as defined in claim 1, wherein the port at the first end of the passageway defines a flow axis oriented radially with respect to an elongated axis of the housing.

4. A syringe as defined in claim 1, wherein the port at the second end of the passageway defines a flow axis oriented approximately parallel to an elongated axis of the housing.

5. A syringe as defined in claim 1, wherein the housing is substantially cylindrical.

6. A syringe as defined in claim 1, further comprising a threaded fitting mounted to the housing at the second end of the axially-elongated fluid passageway.

7. A syringe as defined in claim 1, wherein the plunger defines a tapered surface at a leading end thereof, and the housing further comprises an aperture located at the second end of the passageway and formed in fluid communication with the second fluid port for receiving the leading end of the plunger and forming a substantially fluid-tight seal.

8. A syringe as defined in claim 1, wherein the elongated housing defines an axially-extending interior wall, and the axially-elongated fluid passageway is formed, and further extends between the plunger and the axially-extending interior wall.

9. A syringe as defined in claim 1, wherein the syringe defines an axially-elongated housing, the first fluid port is located at approximately one end of the housing, and the second fluid port is located at approximately an opposite end of the housing.

10. A syringe comprising:

an elongated hollow housing;

a plunger slidably received through one end of the housing and spaced inwardly from an interior wall of the housing, the plunger being movable within the housing to move fluid into and out of the housing;

at least one first fluid port located at approximately one end of the housing and permitting the flow of fluid and gas into and out of the housing;

at least one second fluid port connected in fluid communication with the at least one first fluid port, and located at approximately an opposite end of the housing relative to the first fluid port, wherein the plunger is movable between the first and second fluid ports for moving fluid through at least one of the first and second fluid ports and into and out of the housing;

means defining an unobstructed fluid-flow path between the plunger and interior wall of the housing for maintaining the at least one first fluid port in fluid communication with the at least one second fluid port with the plunger located between the first and second fluid ports, and for allowing gas within the housing to flow out through at least one of the first and second fluid ports to thereby prevent an accumulation of gas within the housing; and means for sealing mounted on the housing at approximately a first end of the unobstructed fluid-flow path.

11. A syringe as defined in claim 10, wherein the means for maintaining the first fluid port in fluid communication with the second fluid port and allowing gas to flow out through at least one of the ports to thereby prevent an accumulation of gas within the housing includes an axially-elongated passageway defined between the plunger and an interior wall of the housing, and extending between and coupled in fluid communication with the first and second fluid ports.

12. A syringe as defined in claim 11, wherein the housing defines an approximately cylindrical interior surface, and the axially-elongated passageway is formed between the plunger and the approximately cylindrical interior surface.

13. A syringe as defined in claim 10, wherein the plunger defines a solid exterior surface.

14. A syringe as defined in claim 10, wherein the means for sealing comprises at least one seal fixedly mounted at approximately one end of the housing, and defining an aperture with the plunger slidably received therethrough forming a substantially fluid-tight seal between the plunger and housing.

15. A syringe comprising:

an elongated housing defining a side wall, and an axially-elongated fluid passageway having a first end and a second end and extending through a substantial portion of the housing in an axial direction thereof;

a first fluid port located at approximately the first end of the passageway and coupled in fluid communication therewith for permitting the flow of fluid and gas into and out of the passageway;

a second fluid port located at approximately the second end of the passageway and coupled in fluid communication with the passageway and the first fluid port for permitting the flow of fluid and gas into and out of the passageway;

a plunger slidably received and movable through the housing between the first and second fluid ports for moving fluid into and out of the housing, wherein the axially-elongated passageway defines an unobstructed fluid-flow path connecting the first and second fluid ports in fluid communication with each other with the plunger located therebetween, to thereby allow gas within the housing to flow out through at least one of the first and second fluid ports and prevent an accumulation of gas within the housing; and a seal fixedly mounted within the housing and located at approximately the first end of the axially-elongated fluid passageway.

16. A syringe as defined in claim 15, wherein the seal at the first end of the axially-elongated fluid passageway comprises at least one o-ring.

17. A method for preventing gas from accumulating within a syringe, wherein the syringe includes an elongated hollow housing, first and second fluid ports axially spaced relative to each other on the housing and connected in fluid communication with a hollow interior of the housing, a plunger slidably mounted within the hollow interior of the housing and movable between the first and second fluid ports for moving fluid through at least one of the ports and into and out of the housing, and an axially-elongated passageway formed between the plunger and an interior wall of the housing, and extending between and connecting the first and second fluid ports in fluid communication with each other with the plunger located between the first and second fluid ports, the method comprising the steps of:

introducing fluid into the hollow interior of the housing through at least one of the first and second fluid ports upon moving the plunger in a first direction between the first and second fluid ports;

directing gas within the fluid introduced into the hollow interior of the housing through the axially-elongated passageway and out of the housing through at least one of the first and second fluid ports;

directing fluid out of the housing through at least one of the first and second fluid ports upon moving the plunger in a second direction opposite the first direction between the first and second fluid ports; and providing a seal mounted on the housing and located at approximately one end of the axially-elongated fluid passageway adjacent to one of the first and second fluid ports.

18. A method as defined in claim 17, further comprising the steps of mounting the syringe with one of the fluid ports located higher than the other fluid port, and directing any gas and fluid out of the housing through the higher fluid port.

19. A method as defined in claim 17, further comprising the steps of introducing fluid and gas into the hollow interior of the housing through one of the fluid ports, and directing fluid and gas out of the hollow interior of the housing through the other of the fluid ports.

* * * * *